(12) United States Patent
Wolf et al.

(10) Patent No.: US 7,524,681 B2
(45) Date of Patent: Apr. 28, 2009

(54) RAPID ASSAY FOR BIOLOGICAL SUBSTANCES USING FTIR

(76) Inventors: Andreas Wolf, Im Herstel 19, 55218 Ingelheim (DE); Ralf Masuch, Schusterstrasse 31, 79098 Freiburg (DE); Robert Seidel, Hauriweg 14, 79110 Freiburg (DE)

(*) Notice: Subject to any disclaimer, the term of this patent is extended or adjusted under 35 U.S.C. 154(b) by 792 days.

(21) Appl. No.: 10/466,848

(22) PCT Filed: Jan. 22, 2002

(86) PCT No.: PCT/EP02/00589

§ 371 (c)(1),
(2), (4) Date: Nov. 18, 2003

(87) PCT Pub. No.: WO02/057753

PCT Pub. Date: Jul. 25, 2002

(65) Prior Publication Data

US 2004/0092027 A1    May 13, 2004

(30) Foreign Application Priority Data

Jan. 22, 2001    (DE) ................. 101 02 743

(51) Int. Cl.
*G01N 33/50* (2006.01)
*G01N 21/35* (2006.01)
*G01J 3/42* (2006.01)

(52) U.S. Cl. .................. 436/171; 436/43; 436/52; 436/63; 436/64; 436/65; 436/86; 436/91; 436/97; 436/98; 436/175; 436/177; 436/811; 436/812; 436/813; 436/814; 250/343; 356/51

(58) Field of Classification Search ............. 436/43, 436/52, 63–65, 86, 91, 97–98, 171, 175, 436/177, 811–814; 250/343; 356/51
See application file for complete search history.

(56) References Cited

U.S. PATENT DOCUMENTS

| 5,473,160 A | * | 12/1995 | Eysel et al. ........... 250/339.12 |
| 5,605,838 A | * | 2/1997 | Backhaus et al. ............. 436/34 |
| 5,734,587 A | * | 3/1998 | Backhaus et al. ............. 702/25 |
| 5,772,606 A | * | 6/1998 | Ashibe et al. ............... 600/573 |
| 5,817,007 A | * | 10/1998 | Fodgaard et al. ............ 600/322 |

OTHER PUBLICATIONS

Moss, D. et al, European Journal of Biochemistry 1990, 187, 565-572.*
Shaw, R. A. et al, Rheumatology international 1995, 15, 159-165.*
Eysel, H. H. et al, Biospectroscopy 1997, 3, 161-167.*
Werner, G. H. et al, SPIE 1998, 3257, 35-41.*
Heise, H. M. et al, Fresenius' Journal of Analytical Chemistry 1998, 362, 141-147.*

(Continued)

*Primary Examiner*—Arlen Soderquist
(74) *Attorney, Agent, or Firm*—Weingarten, Schurgin, Gagnebin & Lebovici LLP (57) ABSTRACT

The present invention relates to a method for determining the condition of a biological fluid by recording the IR spectrum of a sample of the biological fluid. To this end, the biological fluid can be examined in its native form. The method of the invention is usable, for example, for detecting pathological conditions in organisms.

22 Claims, 7 Drawing Sheets

OTHER PUBLICATIONS

Liu, K.-Z. et al, American Journal of Obstetrics and Gynecology 1999, 180, 696-702.*

Petrich, W. H. et al, SPIE 2000, 3918, 91-96.*

Klug, D. D. et al, Review of Scientific Instruments 1988, 59, 767-771.*

Hoffmann, M. M. et al, Review of Scientific Instruments 2000, 71, 1552-1556.*

White, A. J. et al, Biochemical Journal 1995, 306, 843-849.*

Hinsmann, P. et al, Applied Spectroscopy 2001, 55, 241-251.*

* cited by examiner

RAPID ASSAY FOR BIOLOGICAL SUBSTANCES USING FTIR

The present invention relates to a method for determining the condition of a biological fluid by recording the IR spectrum of a sample of the biological fluid. By this method, the biological fluid can be examined in its native form. The method of the invention can be used, for example, to detect pathological conditions in organisms.

Various diseases can currently be detected with sufficient reliability only by use of costly tests that, in addition, are quite time-consuming. Thus, in the event of a myocardial infarction (heart infarction) a diagnosis must be made in the shortest possible time. There is a sudden onset of myocardial necrosis, namely the destruction of a circumscribed heart muscle region, which can be diagnosed by no more than one day after the infarction based on the increase in specific enzymes [CK isoenzyme, CPK, semispecific enzymes, LDH (alpha-hpdh)]. In many cases, however, mild myocardial infarctions, in particular, are difficult to diagnose so that the required treatment is not provided and later a more severe myocardial infarction takes place. This can be prevented by a timely and reliable diagnosis. Moreover, until now a reliable result for some diseases could be obtained only by performing the test post mortem.

For example, reliable tests for detecting prion diseases, for example for diagnosing BSE (bovine spongiform encephalopathy) or Creutzfeld-Jacob syndrome, can be performed only on dead animals or humans, particularly by microscopic examination of brain sections or by costly histochemical antibody tests. Hence, reliable results concerning the spread of the pathogens can be obtained only after the outbreak of the disease. Moreover, these tests are time-consuming and require considerable application of highly qualified personnel and are thus very costly.

Hence, an urgent need exists for reliable tests in the case of the aforesaid diseases, particularly prion diseases, as well as for a great number of clinically relevant changes in body conditions, tests that can be performed in simple fashion on the living organism without procedures for obtaining the samples to be analyzed that would be life-threatening to the animals or humans.

EP-A-0 644 412 discloses a method for analyzing clinically relevant liquid samples and sample suspensions that comprises the recording of infrared spectra of dried samples of the liquids or suspensions to be examined and their evaluation by use of multiparameter evaluation procedures. The evaluation procedure assigns or classifies the samples to be analyzed to classes. The evaluation procedure is calibrated with samples belonging to known classes thus adapting the parameters of the evaluation procedure in a manner such that samples of unknown classification can be assigned to classes. In particular, according to EP-A-0 644 412, infrared spectra are recorded on a dried film of the sample.

This spectroscopic method, however, has the inherent drawback that the samples must be dried for the analysis, meaning that the recorded spectra are spectra of non-native, non-homogeneous samples. Hence, additional processing steps for sample preparation are required, said steps being more time-consuming and making automation of the procedure much more difficult, and information that can only be provided by a sample in its native condition is lost. Moreover, this method is characterized by a high classification or assignment error rate. In particular, in the case of epidemiologically significant pathological conditions such as BSE, however, a reliable classification resulting in a positive or negative finding is critical.

Thus, the object of the present invention is to provide a novel system for determining the condition of biological fluids, for example of body fluids in organisms that is suitable, for example, for detecting pathological conditions in living animals or humans and that avoids the drawbacks of known IR methods. Because of the need for many samples, particularly for clinical diagnosis, according to the invention it is necessary to provide a method which makes possible a high sample throughput with good reproducibility.

This problem is solved by the embodiments of the present invention characterized in the claims.

In particular, the invention provides a method for determining the condition of a biological fluid, said method comprising the steps of
(a) providing several native samples of the biological fluid, the condition of the biological fluid in each sample being known;
(b) recording the IR (infrared) spectra of the native samples of step (a);
(c) subjecting the IR spectra of step (b) to a multiparameter analytical procedure and selecting the classification or assignment parameters that will ensure a reliable assignment of the samples to known conditions;
(d) storing the classification parameters obtained in step (c);
(e) providing a native sample of a biological fluid the condition of which is unknown;
(f) recording at least one IR spectrum of the native sample of step (e);
(g) subjecting the IR spectrum of step (f) to a multiparameter analysis and
(h) comparing the condition parameters of the IR spectrum of the unknown sample with the condition parameters of the IR spectra of the known samples stored in step (d), wherein the IR spectra in steps (b) and (f) are recorded with the aid of a measuring cell with a path length of not more than 30 μm.

The expression "biological fluid" includes all fluids containing biologically relevant substances. The method of the invention is preferably applied to body fluids of organisms. Examples of such body fluids are blood, blood plasma, blood serum, hemolysate, spinal fluid, urine, lymph, synovial fluid, saliva, sperm, amniotic fluid, lacrimal fluid, cyst fluid, sweat gland secretion and bile. Moreover, the expression "biological fluid" also includes suspensions of culture cells, bacteria and viruses as well as medium supernatants and lysates obtained from cultures of the aforesaid cells, bacteria or viruses. By applying the method of the invention to the aforesaid cells, bacteria or viruses, these organisms or pathogens can be classified. For example, an unknown sample is assigned to the presence of a certain cell type, a certain bacterial strain or a certain viral strain. In this manner, for example, a certain bacterial strain present in a suspension or in a medium or in some other fluid can be differentiated from several other bacterial strains.

The term "organism" comprises individual cells, such as prokaryotic and eukaryotic cells, as well as multicell organisms, particularly plants, animals and humans. Preferred organisms are selected from the group consisting of *Bos taurus, Gallus gallus, Maleagris gallopavo, Mus musculus, Ovis ammon, Rattus norwegicus, Sus scrofa* (in general: sheep, chicken, hog) and *Homo sapiens*.

The expression "condition of a biological fluid" comprises all values of parameters of the biological fluid in question. These fluid parameters can be of a chemical or physical nature, for example pH, ion concentrations, redox potentials etc. Preferred chemical parameters comprise, for example, the concentration or the presence or absence of biological substances, such as proteins, nucleic acids, fats and sugars. Other chemical parameters are the concentration of pharmaceutically active substances in the biological fluid in question. By "pharmaceutically active substances" are meant, for example, all pharmaceuticals or their pharmacologically active ingredients as well as drugs. Other preferred parameters of biological fluids that can be determined by the method of the invention are the presence or absence of pathogens. The pathogens can be, for example, eukaryotes, for example fungi, or prokaryotes, for example bacteria. Other pathogens that can be detected according to the invention comprise viruses and protein-like pathogens, particularly prions.

The method of the invention can be used, for example, to detect pathological conditions, which means that the sample of a body fluid of an organism is assigned to the condition "ill" or "with findings" or to the condition "not ill" or "without findings". Examples of pathological conditions that can be detected with the aid of the method of the invention comprise diabetes, arthritis, elevated (or reduced) cholesterol level, anemia (for example sickle cell anemia), cancer, liver diseases (for example hepatitis), AIDS, kidney diseases, tissue destruction (for example, myocardial infarction), neurodegenerative diseases, such as Alzheimer's disease, Parkinson's disease, transmissible spongiform encephalopathy (TSE) such as BSE, autoimmune diseases such as multiple sclerosis (MS), allergies, urticaria and allergic asthma. Pathological conditions can also be caused by (prohibited) feed and/or feed additives used in the husbandry of animals, for example that of hogs and chickens.

To prepare the native sample or samples in the aforesaid steps (a) and/or (e), the body fluid is treated before analysis, for example by freeing it of particulate constituents. For example, before recording the IR spectra, blood is treated to provide serum. Thus, an outstanding feature of the method of the invention is, among other things, that the recording of the IR spectra in the aforesaid steps is carried out on homogeneous samples. The removing of the body fluid from particulate constituents can comprise, for example, a centrifugation and/or filtration or ultrafiltration through a membrane of appropriate pore size.

For example, by filtration (particularly ultrafiltration), centrifugation and/or dialysis, it is possible, for example in the case of detection of a pathological condition, to obtain body fluid fractions that are optimized for the disease, namely that provide the largest possible disease-specific spectral change. In this manner, it is possible to reduce appreciably the total, highly complex spectral information thus offering the possibility of obtaining information about the clinical picture with the aid of data analysis. An example of complexity reduction is electrochemically induced difference analysis wherein electrodes are integrated with the measuring cell. In this manner, with the aid of an applied potential, certain constituents, particularly biomolecules such as proteins (for example heme proteins) can be selectively oxidized or reduced depending on their midpoint potential. The changes induced in this manner (for example, changes of an electronic or structural kind) can be used as recognition features. By varying the applied potential, it is thus possible to selectively modify various constituents. Thus, by electrochemically induced difference analysis based on the selection of only redox-active components of the body fluid and by appropriate selection of the potential range, it is possible to achieve an advantageous reduction of the complex spectral information, the detection sensitivity being increased by the fact that changes in individual functional groups of biomolecules can be determined. For example, by electrochemically induced difference spectra of red blood cells, hemolysate or a hemoglobin fraction, the protein defects, for example the genetically induced amino acid difference in sickle cell anemia, can be detected in the hemoglobin and identified as disease by a comparison based on multiple parameter analysis. This detection is optimized for the midpoint potential specific for hemoglobin.

With the aid of a multiparameter analytical procedure, the total absorption spectra and the induced difference spectra can be used for the diagnosis of diseases in complementary manner or individually.

The aforesaid preparation steps, however, do not change the "native" character of the samples. Hence, the analytical sample for the method of the invention is characterized in that the constituents contained therein are present under conditions, particularly as regards the water content, salt content, pH etc., and optionally temperature, which are the same as those of the body fluid in the organism from which the sample was taken. This means, for example, that the biomolecules (protein, nucleic acids etc.) contained in the body fluid in question and that are essential for the determination of the condition are not in a denatured state. This is in contrast to the method described, for example, in EP-A-0 644 412, for which a fluid sample must be dried on a carrier material before the IR analysis is performed.

In a preferred embodiment of the method of the invention, the recording of the IR spectra in the aforesaid defined steps (b) and (f) is carried out by means of a spectrometer designed for Fourier transform infrared spectroscopy (FTIR), which enables fast recording and evaluation of the spectra. The FTIR spectrometer can be coupled, for example, with an IR microscope. The IR spectra can be recorded by the transmission and/or reflection technique.

The information content of IR spectra of the body fluids analyzed according to the invention is particularly high in the middle IR range. For this reason, the recording of the IR spectra in step (b) and/or step (f) of the aforedefined method is preferably done at a wave number from 400 to 7,000 cm$^{-1}$ and particularly from 700 to 1,900 cm$^{-1}$.

According to the invention, the IR spectra of the native samples recorded in step (b) for which the condition of the biological fluid, for example the body fluid of an organism, is known, are subjected in step (c) to a multiparameter analytical procedure. To this end, the values obtained by recording the IR spectrum in question are first digitized. The digitized spectrum is then subjected to a multiparameter analytical procedure. Multiparameter analytical procedures that can be used according to the invention are, for example, multivariate data analysis methods, such as linear discriminatory analyses, neuronal networks and cluster analyses, which are commercially available as software programs.

In step (c) of the method of the invention, the multiparameter analytical procedure is prepared, namely calibrated, by processing the information contained in the IR spectra of the native samples of the body fluids of the organisms for which the condition is known. By means of the multiparameter analysis, classification parameters are obtained from the data records of the IR spectra ensuring a reliable classification or assignment of the samples in question to the known conditions. According to the invention, to calibrate the multiparameter analytical procedure, several IR spectra of samples, for example from 5 to 1000 and preferably from 50 to 300, are analyzed by the multiparameter analytical procedure with the underlying body fluid being known to show, for example, condition A. Correspondingly, an identically large number of IR spectra for which the underlying body fluid shows, for example, condition B, is analyzed. The number of spectra per condition needed for calibrating the multiparameter analytical procedure depends especially on the extent to which the spectra for the various conditions differ among themselves. In general, however, it is preferred to calibrate the multiparameter procedure with a rather large number, for example more than 100, spectra per condition, because the classification error rate decreases with the size of the data set available for the multiparameter analytical procedure. As stated above, the multiparameter analysis of the IR spectra is preferably carried out with the aid of software-controlled data processing. By storing the classification parameters obtained, preferably in an electronic data carrier, said parameters are then available for a comparison with the corresponding data records of an IR spectrum of a sample of a body fluid the condition of which is unknown.

In this manner, by the method of the invention, a native sample of a body fluid of unknown condition is measured, subjected to the multiparameter analytical procedure and, by comparison of the condition parameters of the IR spectrum of the unknown sample with the previously obtained and stored condition parameters of the IR spectra of the known samples, is assigned to a condition, for example condition A or condition B. By suitable selection of the reference conditions it is, of course, also possible by the method of the invention to set up calibration series (for example, the concentration of a substance from 0 to n concentration units corresponding to conditions A to Z), allowing, for example, quantitative determinations. Hence, the method of the invention, by appropriate calibration of the multiparameter analytical procedure, also provides, for example, information about the degree or stage of a pathological condition, for example by how much the cholesterol level deviates from the normal value or what stage of cancer is present.

Suitable apparatus for carrying out the method defined in the foregoing is, for example, an analytical apparatus comprising an FTIR spectrometer, related pumps and a suitable measuring cell, designed for recording FTIR spectra of a native, fluid sample. Because according to the invention the IR spectra of native samples are recorded, the recording in the aforedefined step (b) and/or step (f) is carried out with the aid of a measuring cell with a path length from 1 to 30 µm, particularly from 3 to 12 µm and most preferably not more than 10 µm. The selection of the optimal path length for transmission cells for aqueous samples is described, for example, by Rahmelow, K. and Huber, W. (1997) in Appl. Spectrosc. 51, 160-170. For the recording of the IR spectra according to the invention, the short path length is required especially because when the optical path length exceeds 12 µm, the water present in biological fluids causes the range of total absorption to increase, and above 30 µm the information content becomes very small for the method of the invention.

Suitable optical materials for the method of the invention are, in general, all materials that are transparent to IR in the indicated wave number range or partial range, preferably calcium fluoride ($CaF_2$), barium fluoride ($BaF_2$) zinc selenide (ZnSe), silicon (Si), germanium (Ge) and thin polymer films. Optionally,the materials can be coated with thin, water-insoluble layers of, for example, Parylene, PTFE or PE. In this manner, special properties can be imparted to the short-path cell. For example, such materials can be used to reduce the interaction between the window material or cell material and the biological sample or to isolate water-soluble window materials from the water-containing sample solution. This provides a larger selection of optical materials and thus a wider spectral range. Therefore, water-soluble potassium bromide (KBr), for example, can also be used as window material.

Moreover, electrodes can be integrated with the cells, for example in the form of microstructured networks, to permit electrochemically induced difference analysis (difference spectroscopy). Such measuring cells are described, for example, by Moss, A. D., Nabedryk, E., Breton, J. and Mäntele, W. (1990) Eur. J. Biochem. 187, 565-572.

The three following embodiments of one-piece short-path cells for fluids can be used for the analytical methods:

Type 1: One-piece microstructured flow-through cell

Such cells are commercially available and have the following characteristics:

High pressure resistance (for example 10-100 bar). This is advantageous in case of high flow resistance during the filling of flow-through cells (particularly those with path lengths ranging from 1 to 15 µm);

Small filling volume (0.05 to 3 µL); hence only very small sample quantities are suitable;

Automated high throughput is possible; the filling and rinsing of the cells can be accomplished very quickly;

Fast pressure relaxation (<10 ms); needed for high sample throughput;

Such cells retain a constant path length during the sample analysis despite the varying pressure conditions. The deviation remains below the detection limit of the IR analysis and, hence, does not produce interfering signals. The reproducibility of the method of the invention is thus extremely improved;

Integration with microstructured electrodes is possible.

By the integration of electrodes with the IR measuring cell, for example of microstructured electrodes with the one-piece microflow-through cell, it is possible to impart to the method of the invention the following additional advantages:

Complexity reduction for samples with redox-active components in the body fluid can be achieved. Data analysis based on the total spectrum and the detailed (high-resolution) electrochemically induced difference spectrum is possible providing new (additional) spectral information.

By integration of the cell with microstructured electrodes, scannable potential intervals can be evaluated for spectral changes specific for a potential interval.

It is possible to evaluate a potential range with maximum disease-specific spectral change optimized for a specific disease.

Type 2: One-piece microstructured diffusion mixing cell

Such measuring cells are known from the prior art and have the following properties:

No cleaning is necessary, because the cells are discarded after use (single-use cells);

Constant path length;

The sample volume needed is small (<1 µL, for example 50-200 nL);

Fast pressure relaxation and high pressure resistance are not needed, because:

single-use, disposable cells or array are used (no time-consuming rinsing and cleaning is necessary; handling is simple when working with pathogenic biomaterial (for example with samples assigned to safety class S2);

filling occurs by capillary force;

Suitable for "point-of-care" use.

Type 3: one-piece capillary force short-path cell

A measuring cell of this type is described in DE 197 39 126 and has the following properties:

Small sample volume (<5 µL);
Fast relaxation and high pressure resistance are not needed, because
the cell is of the single-use, disposable type;
filling occurs by capillary force;
Integration with microstructured electrodes is possible.

According to a preferred embodiment of the method of the invention, the recording and evaluation steps are fully automated for a high throughput of several thousand, for example 5000, recordings and evaluations per day per instrument. To this end, the method of the invention can be carried out with the aid of a measuring apparatus in which the individual components such as pumps, sampling loops, control valves, mixers etc., are designed for operation with very small volumes and high pressures, such as those encountered, for example, in high pressure liquid chromatography (HPLC). The control of these individual components is preferably accomplished by computer. The use of HPLC components in conjunction with a microflow-through cell having a path length of 1 to 15 µm requires very small samples of preferably <20 µL. More preferable are flow-through systems requiring samples from 1 to 10 µL and particularly 5 µL.

In carrying out the method indicated above, particularly when using HPLC components, high pressures from 1 to 100 bar are generated depending on the speed at which the measuring cell is filled. To ensure the reproducibility of the method of the invention and thus the reliable classification of the condition of the biological fluid being examined, the measuring cell during the recording of the spectrum shows a path length deviation of preferably less than 1 nm from the native path length despite the varying high pressure load during filling and rinsing of the cell.

In particular, the method of the invention is carried out, for example, in an aforesaid flow-through apparatus, as follows. With the pump running, the samples, for example, blood serum, blood plasma etc., are fed via a sampling loop valve, to a transport medium (for example water or an aqueous buffer solution) and then transported into the FTIR measuring cell. Once the sample is in the measuring cell, the flow is stopped and the FTIR spectrum of the sample is recorded. The cell is then rinsed with transport medium. By use of sampling loop valves, the sampling loop can be refilled even while recording is being carried out. In this manner, the sample throughput is limited almost exclusively by the duration of the recording time (in the case of FTIR recording as a rule 15 to 30 seconds), as a result of which the system is particularly well suited for automation for a large number of samples.

As indicated in the foregoing, the above system is suitable for manual, semiautomatic as well as fully automatic execution of the method of the invention. In the case of automated, high sample-throughput, the above recording system is preferably computer-controlled and fitted with HPLC-compatible components. In such a system, the sample can be fed, for example, from standardized microtiter plates.

In an automated version of the method of the invention, the recording of the IR spectra is preferably done with the aid of the aforesaid one-piece, microstructured flow-through cell into which can optionally be integrated electrodes for carrying out an electrochemically induced difference analysis of the biological fluid.

An important application of the method of the invention for determining the condition of a body fluid of an organism consists of determining the concentration or composition of, for example, a body fluid, for example the effect of pathogens or prohibited additives in animal feed used in hog or cattle husbandry, on the blood or blood serum of humans, hogs and *Bos taurus* (cattle). A specific example in this case is the determination of the concentration, or the detection of the effects of the presence or absence of prions in a body fluid, for example in a body fluid such as, for example, the blood or blood serum of *Bos taurus* (cattle).

Thus, one embodiment of the method of the invention constitutes a rapid test that is based not on the direct detection of a pathogen, substance or active ingredient, but on the recognition of the composition of body fluids (for example blood count/blood composition), which has been changed, for example, by autoimmune reactions (for example, multiple sclerosis), food additives, amyloids (Alzheimer's disease) or prions (TSE) that affect the metabolism of the diseased animal/human. According to the invention, a rapid test can be developed for BSE that is based not on the direct detection of the BSE pathogen, but on the recognition of the composition of body fluids (for example, of the blood count), said composition being modified by the presence of prions that affect the metabolism of the diseased animal.

In contrast to the tests thus far performed on dead animals, the method of the invention can be performed on living organisms and, moreover, does not involve significant procedures. For example, compared to the currently available BSE test for which an estimated six to eight hours per test is required, the method of the invention involving up to 5000 determinations per day per apparatus can be carried out very quickly. By avoiding high labor costs and large expenses, considerable cost reduction can be achieved for the individual analyses.

The multiparameter analytical procedure used according to the invention to assign samples to known conditions and for comparison of the unknown sample can regularly be adapted to modified conditions and optimized for constant conditions. For example, in case of the emergence of new variants of a pathogen, that, for example, are not amenable to a conventional antibody test (antibodies reacting only to certain forms of pathogens but not to a modified pathogenic variant), the multiparameter analytical procedure, for example a neuronal network, can be adapted to the modified condition. This prevents false-negative test results, which in highly specific antibody tests often occur as a result of the polymorphism of a pathogen, because thereby a new isoform of the pathogens is often not recognized. By contrast, the method of the invention is not adversely affected by the polymorphism of a pathogen.

Moreover, only very small amounts of sample (<20 µL) are needed, particularly when HPLC components are used.

Furthermore, the analysis of samples in their native state results in a much more reliable classification, namely the avoidance of false-positive and false-negative test results, than do methods involving IR analysis of dried samples, for example dried films of the samples. It is thus possible, particularly in the recognition of epidemiologically significant pathological conditions such as BSE, to achieve a much lower error rate.

In particular, the method of the invention has the following advantages over prior-art methods that involve IR analysis performed on biofilms:

Water plays an essential role in the stabilization of the spatial structure of biomolecules. In the native state, soluble biomolecules are surrounded by a hydrate shell that interacts with the ionic or polar functional groups in a conformation-stabilizing manner. On the inside of the molecular structure, too, water acts by hydrogen bonding on the spatial structure of the biomolecule in a stabilizing and shaping manner. Dehydration in form of dried biofilms can in this case cause critical structural modifications by intermolecular interactions with neighboring molecules.

The native condition of a body fluid and thus the native conformation of the dissolved components prevails for the method of the invention but not for the analysis of dried biofilms. For example, the disease or the change in condition of a body fluid can be caused by the change in conformation of a protein. In this case, a differentiation can lead to detection only by comparison between the native and the pathogenic conformation. In dried biofilms, the native or the pathogenic conformation can be changed or destroyed by the dehydration, which would make differentiation more difficult or impossible.

A biofilm shows different dehydration states depending on the film thickness or the distance from the outer layer. Inside the film the dehydration has progressed to a lesser degree than at the edge. The reason is that water from the interior can reach the outside only slowly by diffusion through the layer above it.

Different dehydration states in a sample lead to different, or different degrees of, intramolecular and intermolecular interactions with neighboring atoms or functional groups, so that a band shift takes place (the absorption maximum is shifted toward another wave number). This means that an absorption peak characteristic for a functional group and the extinction coefficient are dependent on the degree of dehydration. Different dehydration states in a sample therefore result in line broadening because many peaks are slightly shifted relative to one another, which, disadvantageously, provides less spectral information.

Moreover, the sample used for classification purposes must show the same degree of dehydration as was the case for the data records used in the preparation (calibration) of the multivariate data analysis, otherwise different band shifts would prevent unambiguous band classification ("assignment").

Because of the drying process, biofilms have a nonhomogeneous composition. This causes deterioration in analytical reproducibility.

For good reproducibility and a low classification ("assignment") error rate, consistent with the calibration data records, the following parameters must be optimized in the preparation of biofilms:

Duration of drying
Drying gradient
Drying temperature
Coating quantity applied
Thickness of applied coating
Carrier material (wetting)
Film surfaces (for example, curvature, roughness etc.) (important for the transmission/reflection/scattering relationship)
Coating method (for example, there is a difference between a single thick coating application and several thin applications with drying phases between the applications). Otherwise inferior reproducibility and a higher classification error rate will result.

The aforesaid problems concerning analysis of biofilms can be controlled somewhat only by expensive, cost-intensive metering, heat-control and regulation techniques. Hence, prior-art methods are unsuitable for widespread use or for "point-of-care" use.

Also for better reproducibility, the recording of spectra of the samples to be classified should be done by the same recording technique as for the calibration data records. To record spectra of dried biofilms, however, many techniques are in widespread use, for example transmission, reflection or diffuse reflection techniques, which provide data that cannot be compared with sufficient accuracy.

Electrochemical difference analysis is meaningful only when the redox-active components still retain their native conformation, that as a result of the redox process they undergo characteristic, highly specific structural changes (cf. Moss, A. D., Nabedryk, E., Breton, J. and Mäntele, W. (1990) Eur. J. Biochem. 187, 565-572). In biofilms, however, the molecules are in a dehydrated state, so that here one cannot speak of a "native" sample.

For spectrum calibration, a calibration substance is added to the biofilms in most cases. Such calibration is not needed for the method of the invention.

The method of the invention is not affected by the problems of sample preparation explained in the foregoing. The preparation steps for most body fluids (if at all needed) are standardized, and furthermore in relevant organisms the substances dissolved in the body fluid are present in most cases in similar concentrations so that, on the one hand, the native character of the body fluid is retained and, on the other, a direct comparison of the samples is possible. Optionally, it is necessary to standardize the data concerning the path length of the measuring cell used to the path length of the reference measuring cell. Hence, the method of the invention, because of the possibility of establishing multivariate parameter records concerning a particular disease (or the change in condition of a biological fluid) combined with good reproducibility of the analytical technique is eminently suitable for widespread use.

The figures show the following.

FIG. 5 (A) is a graphic representation of the second derivative of IR spectra of the blood serum of five different human patients, and (B) shows the spectra of (A) superposed on one another in the wave number range from 1680 to 1800 $cm^{-1}$.

FIG. 6 (A) shows the absorption spectra of spinal fluid samples from patients with or without multiple sclerosis, and (B) shows the second derivative of these absorption spectra.

Figure 1:
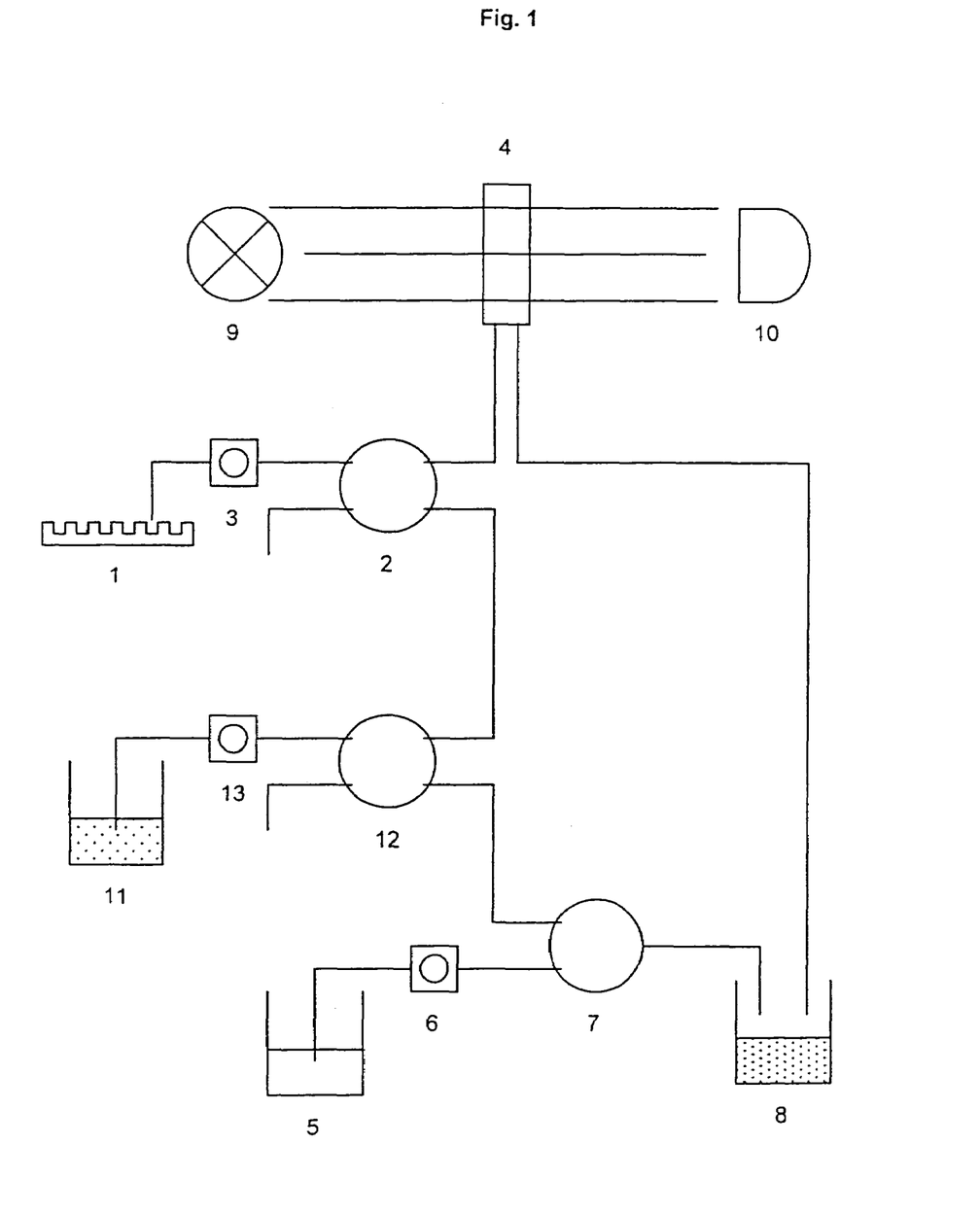
FIG. 1 is a schematic representation of a device suitable for carrying out the method of the invention.

The method of the invention can be carried out, for example, with the device shown in FIG. 1 as follows:

The samples can be supplied manually (semiautomatic system) or from microtiter plates (1) (fully automatic system).
From the supply, the samples are introduced into an injection valve (2).
The samples from the microtiter plates (1) are taken up sequentially through a pump (3).
Through the injection valve (2) the samples are introduced into the flow-through measuring cell (4).
By switching the injection valve (2), the sample is fed into a transport medium (5) (for example, water or an aqueous buffer solution) and then transported into the flow-through measuring cell (4).
The transport medium (5) is driven by an additional pump (6) (preferably an HPLC pump).

When the sample is in the measuring cell (4), the flow of the transport medium (5) is diverted by a control valve (7), for example, to a waste container (8) and thus, the flow through the measuring cell (4) stops.

The measuring cell (4) is integrated with an IR spectrometer (or IR microscope) whereby one or more IR spectra can be recorded. During the recording, there is no flow through the measuring cell (4).

To record the IR spectra, light from an IR light source (9) is made to pass through the sample and is detected by a detector (10).

A reduction or oxidation of the sample is optionally carried out. For different applied potentials, at least one IR spectrum is recorded in each case.

Subsequently, the control valve (7) is reset and the sample is completely rinsed out of the cell (4) with transport medium (5) into a waste container (8).

Optionally, the cell (4), the sampling loop and the lines through which the sample was made to flow are cleaned with a cleaning solution (11), for example SDS/6 M guanidinium hydrochloride. The cleaning solution (11) is preferably introduced through a second injection valve (12) between the control valve (7) and the first injection valve (2) by use of an additional pump (13).

As a rule, after the rinsing [cell (4) is completely filled with transport medium (5)], a reference spectrum in the stopped condition is recorded. To this end, the transport medium (5) serves as a reference that remains constant.

Optionally, the injection valve (2) can be switched before, during and/or after the recording of the sample spectrum, and the sampling loop can be refilled. Preferably, the injection valve (2) is switched before the recording and refilled. In this manner, the sample throughput is limited almost exclusively by the duration of the recording (generally 15-30 seconds), the system thus being suitable for automation for a large number of samples.

The evaluation of the IR spectra obtained is performed by multivariate data analysis.

Finally, the sample is assigned to a group of the multivariate data analysis.

The system is preferably made up of HPLC components.

In the following, the invention will be explained in greater detail by way of nonlimiting examples.

EXAMPLES

Electrochemically Induced Difference Analysis of Hemoglobin

Figure 2:
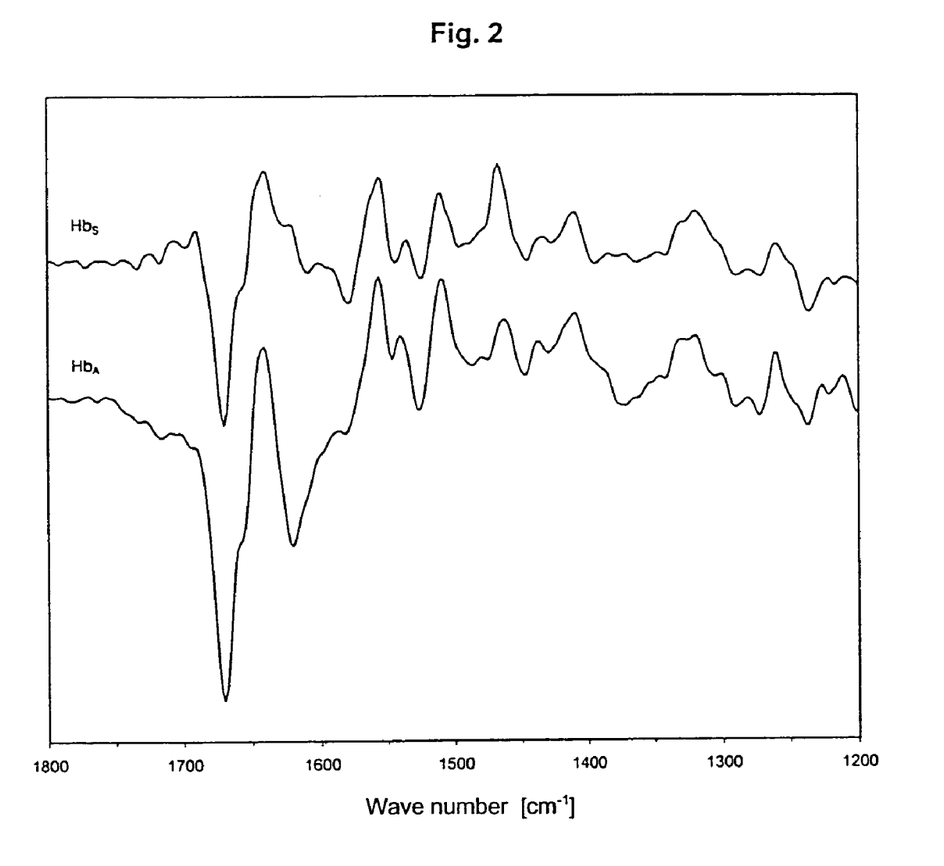
FIG. 2 is a graphic representation of the electrochemically induced FTIR difference spectra of normal human hemoglobin ($Hb_A$) and of sickle cell anemia hemoglobin ($Hb_S$).

Solutions of normal human hemoglobin ($Hb_A$) and sickle cell anemia hemoglobin ($Hb_S$) were prepared. Electrochemically induced difference spectra thereof were recorded by means of an FTIR spectrometer in a short-path cell. The difference spectra are shown in FIG. 2. The two spectra show good agreement in certain absorption ranges. In other ranges, however, a definite difference, characteristic for sickle cell anemia hemoglobin, is recognizable. Thus, the method of the invention provides a rapid and universally usable detection method, for example for diagnostic purposes in the clinical field, because the electrochemically induced difference analysis is applicable to all redox-active substances in biological fluids.

FTIR Analysis of Human Blood Sera

Figure 3:
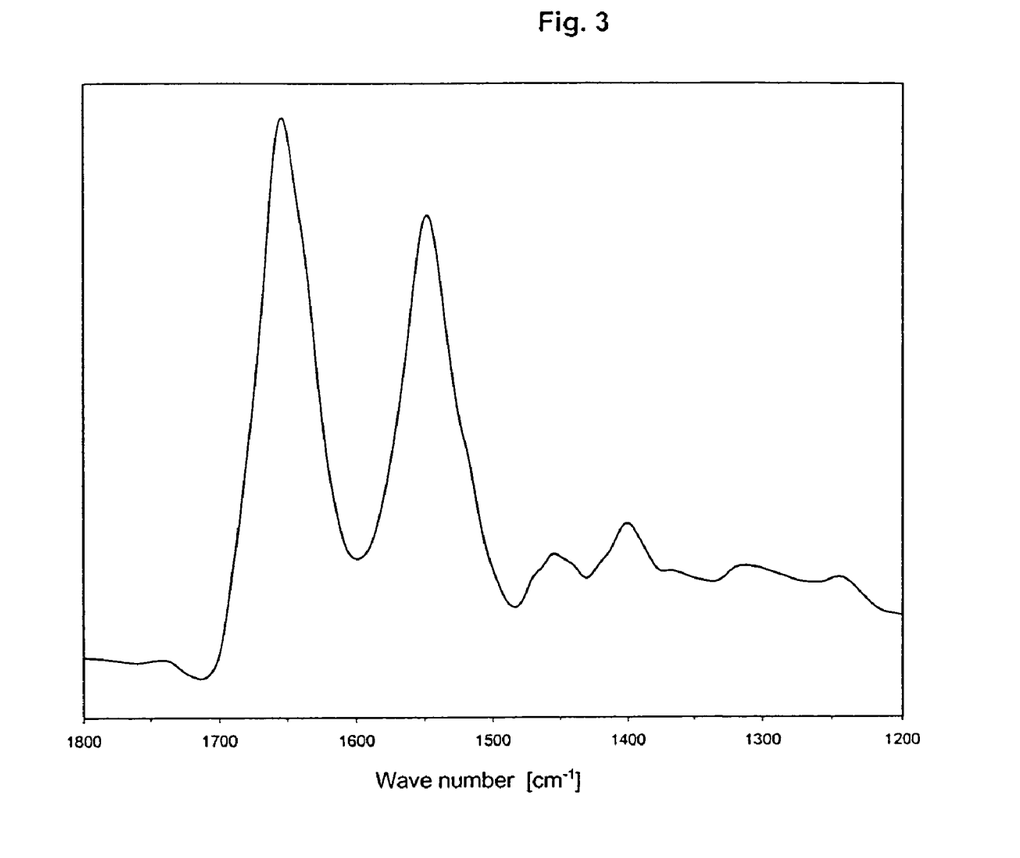
FIG. 3 is a graphic representation of the total IR absorption spectrum of human blood serum. A short-path flow-through cell was used (path length: about 6 μm).

A total absorption spectrum was recorded by means of a short-path flow-through cell (path length 6 µm) (FIG. 3).

Figure 4:
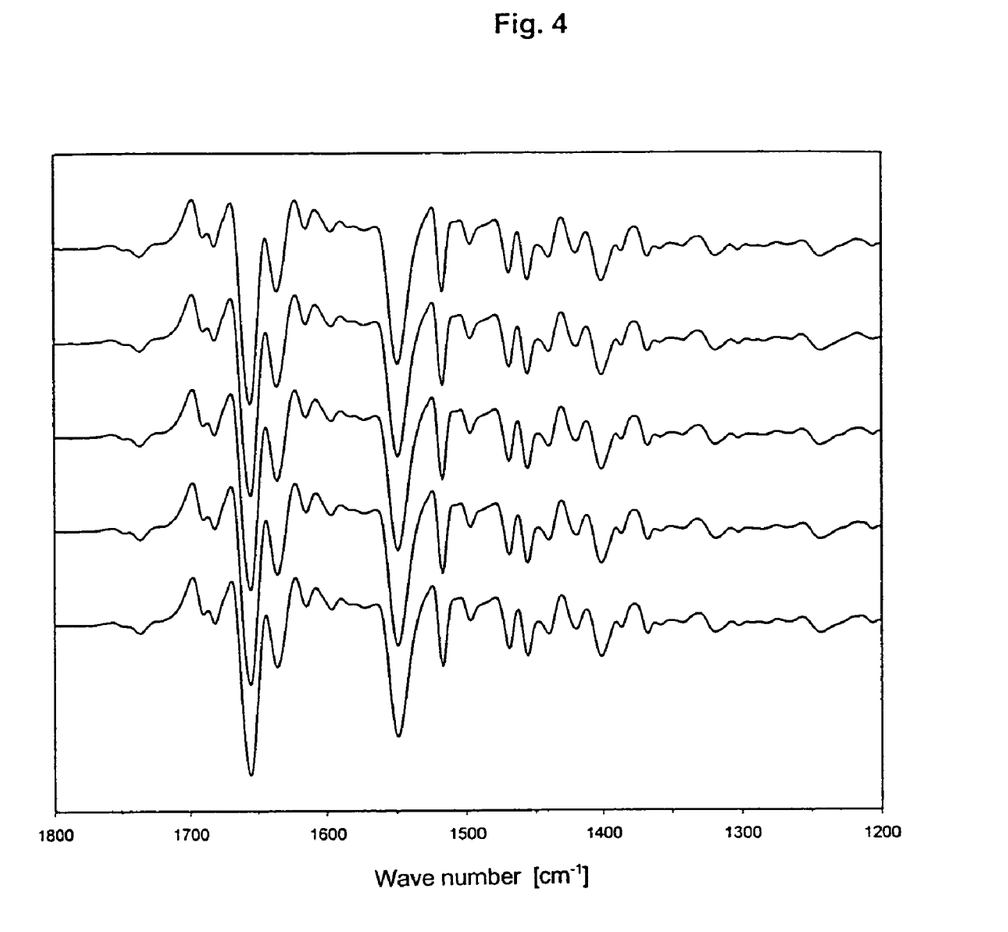
FIG. 4 is a graphic representation of the second derivative of five IR spectra of the blood serum of a human patient.

The reproducibility of the IR spectra (second derivative) was investigated on human blood serum by using the same measuring system. To this end, five samples from the same patient were injected into the measuring apparatus and the spectra were recorded. The spectra in FIG. 4 show outstanding reproducibility, unattainable by analysis of biofilms.

Figure 5:
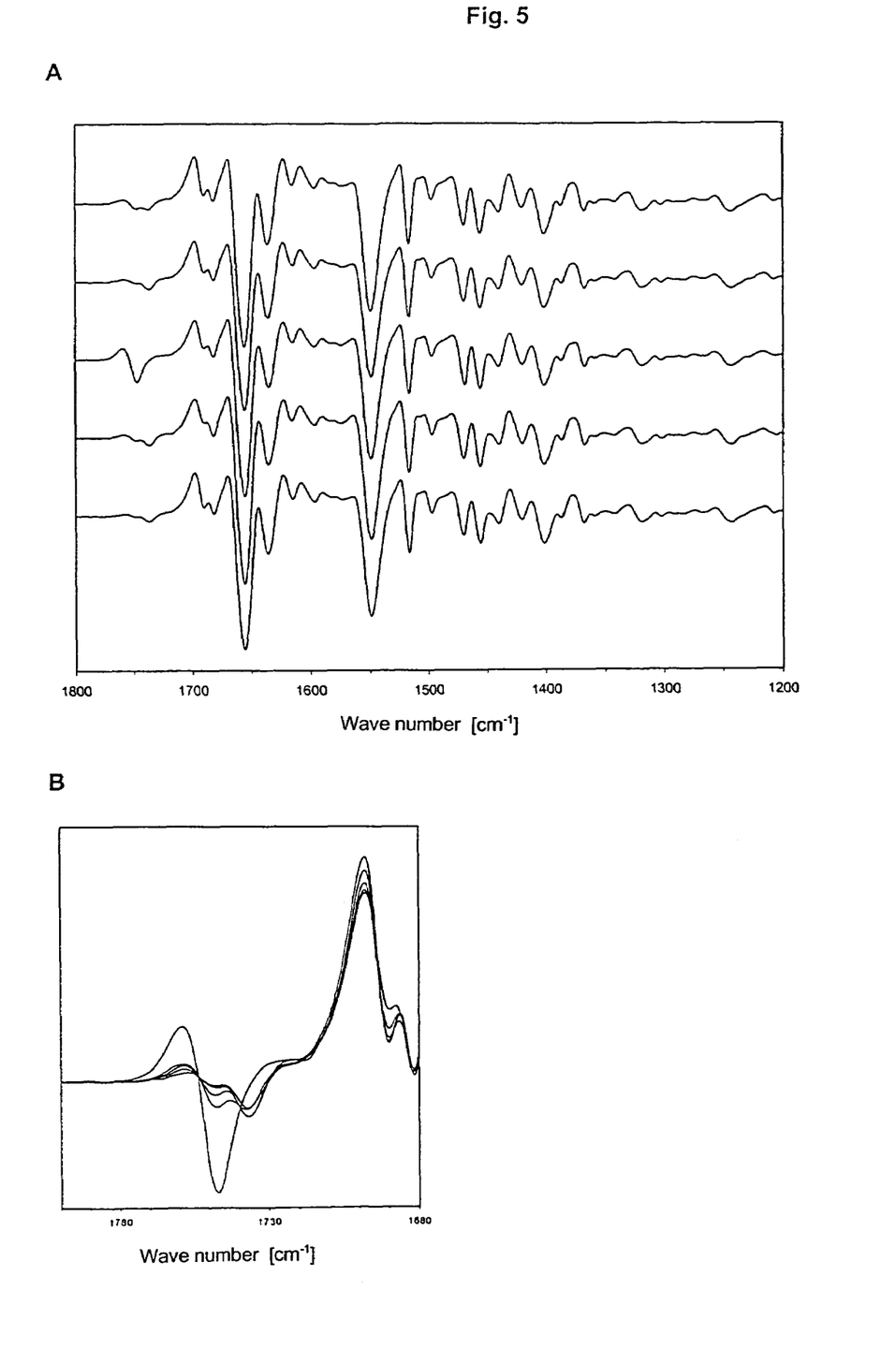

FIG. 5A shows the IR spectra (second derivative) of five different human blood sera, also recorded using the above short-path flow-through cell. As can be seen, the spectra of the samples from different patients show definite differences in certain ranges. This is particularly evident, for example, in the range from 1680 to 1800 $cm^{-1}$ when the spectra are superposed (FIG. 5B).

FTIR Analysis of Samples of Human Spinal Fluid and Serum From Patients With Multiple Sclerosis From an extensive human databank, samples of spinal fluid and serum from patients with multiple sclerosis were analyzed by the method described above. The samples which had been stored frozen—fresh samples can also be used—were subjected to analysis in the thawed, liquid state in an apparatus with a short-path cell. In the simplest case, these samples can be used directly. Optimization can be achieved by appropriate pretreatment of the samples. For the subsequent data evaluation by chemometric methods, the recorded absorption spectra can be used directly, or the second derivative thereof can be used. It may be useful for the evaluation of the spectra to enlarge the spectral range of the recorded spectra to 700 $cm^{-1}$ and to 3000 $cm^{-1}$, because this increases the information content.

Figure 6A:
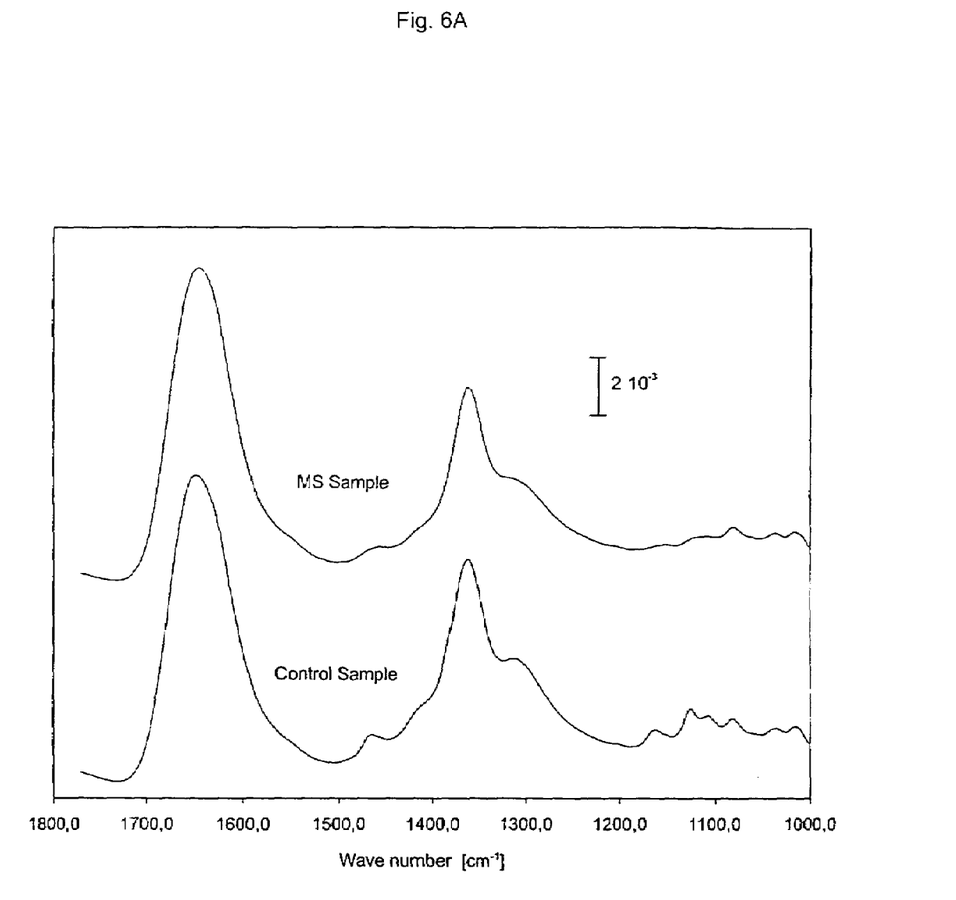
Figure 6B:
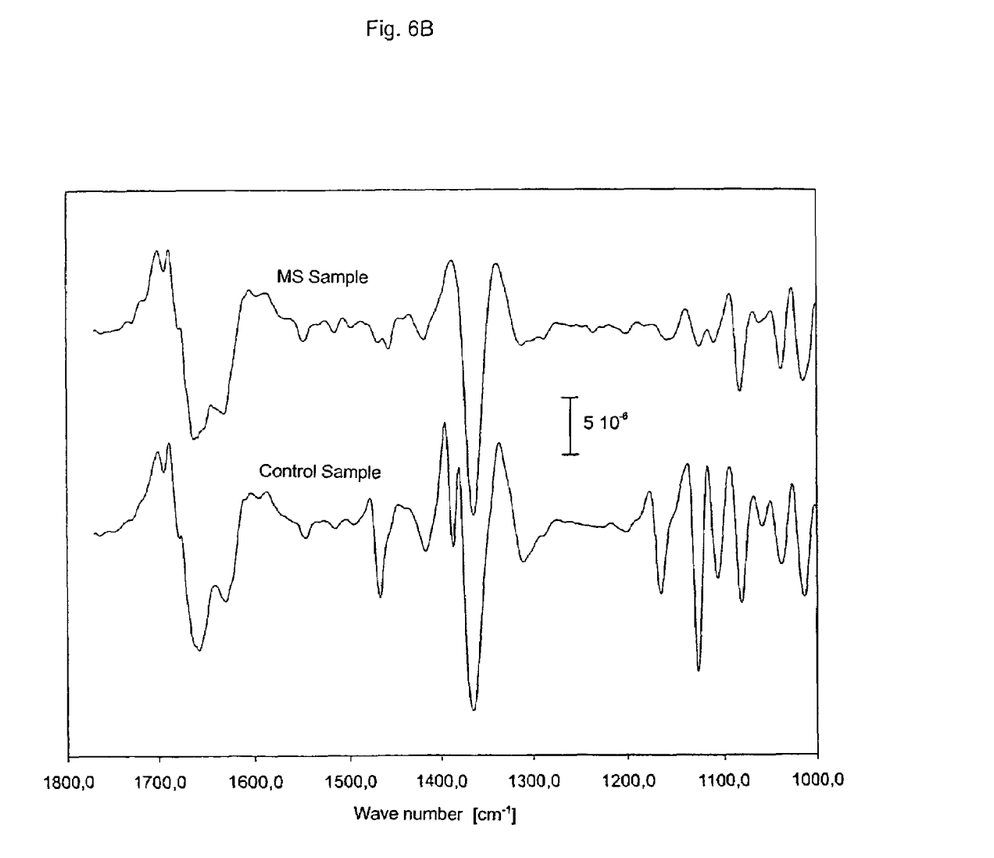

FIGS. 6 (A) and 6 (B), with the example of spinal fluid, show the spectra for patients with and without multiple sclerosis.

The invention claimed is:

1. Method for determining the condition of a biological fluid comprising the steps of
   (a) providing several native samples of the biological fluid, the condition of the biological fluid in each sample being known;
   (b) recording the IR spectra of the native samples of step (a);
   (c) subjecting the IR spectra of step (b) to a multiparameter analytical procedure and selecting the classification parameters that will ensure a reliable assignment of the samples to the known conditions;
   (d) storing the classification parameters obtained in step (c);
   (e) providing a native sample of a biological fluid, the condition of which is unknown;
   (f) recording at least one IR spectrum of the native sample of step (e);
   (g) subjecting the IR spectrum of step (f) to a multiparameter analysis; and
   (h) comparing the classification parameters of the IR spectrum of the unknown sample with the classification parameters of the IR spectra of the known samples stored in step (d), wherein the IR spectra in steps (b) and (f) are recorded under non-flowing and stopped conditions after filling the flow-through measuring cell with said sample or with a transport medium for a corresponding reference measurement, wherein the measuring cell has a path length of not more than 30 µm and a path length deviation of less than 1 nm between any two consecutive measurements requiring filling or rinsing of said measuring cell between said consecutive measurements, which filling or rinsing can cause flow- or pressure-induced path length deviations.

2. Method according to claim 1 wherein the provision of the native sample(s) in step (a) and/or step (e) comprises the homogenization of the biological fluid and/or the freeing of the biological fluid of particulate constituents.

3. Method according to claim 2 wherein:
the recording of the IR spectra in step (b) and/or in step (f) is carried out at a wave number from 400 to 7000 cm$^{-1}$;
the recording of the IR spectra in step (b) and/or in step (f) is carried out with the aid of an FTIR spectrometer and/or FTIR microscope;
the recording of the IR spectra in step (b) and/or step (f) is carried out with the aid of a measuring cell with a path length from 3 to 12 μm;
the multiparameter analytical procedure is a discriminatory analysis, a neuronal network or a cluster analysis;
the measuring cell contains integrated electrodes for
the reduction and/or oxidation of biomolecules in the sample;
the biological fluid is a body fluid of an organism;
the biological fluid is selected from the group consisting of blood, blood plasma, blood serum, hemolysate, spinal fluid, urine, saliva, sperm, lymph, synovial fluid, amniotic fluid, lacrimal fluid, cyst fluid, sweat gland secretion and bile;
the organism is selected from the group consisting of *Bos taurus, Gallus gallus, Maleagris gallopavo, Mus musculus, Ovis ammon, Rattus norwegicus, Sus scrofa* and *Homo sapiens*;
the sample of unknown condition is assigned to a pathological or non-pathological condition and/or to a stage or degree of a pathological condition;
the pathological condition is selected from the group consisting of diabetes, arthritis, elevated cholesterol level, anemia, tissue destruction, cancer, liver diseases, kidney diseases, myocardial infarction, AIDS, allergies, urticaria, allergic asthma, autoimmune diseases, neurodegenerative diseases and TSE;
the pathological condition is caused by feed and/or feed additives used in animal husbandry;
the sample of unknown condition is assigned to the presence of a certain cell type, a certain bacterial strain or a certain viral strain.

4. Method according to claim 1 wherein the recording of the IR spectra in step (b) and/or in step (f) is carried out at a wave number from 400 to 7000 cm$^{-1}$.

5. Method according to claim 1 wherein the recording of the IR spectra in step (b) and/or in step (f) is carried out with the aid of an FTIR spectrometer and/or FTIR microscope.

6. Method according to claim 1 wherein the recording of the IR spectra in step (b) and/or step (f) is carried out with the aid of a measuring cell with a path length from 3 to 12 μm.

7. Method according to claim 1 wherein the multiparameter analytical procedure is a discriminatory analysis, a neuronal network or a cluster analysis.

8. Method according to claim 1 wherein the measuring cell contains integrated electrodes for the reduction and/or oxidation of biomolecules in the sample.

9. Method according to claim 1 wherein the biological fluid is a body fluid of an organism.

10. Method according to claim 9 wherein the organism is selected from the group consisting of *Bos taurus, Gallus gallus, Maleagris gallopavo, Mus musculus, Ovis ammon, Rattus norwegicus, Sus scrofa* and *Homo sapiens*.

11. Method according to claim 9 wherein the sample of unknown condition is assigned to a pathological or non-pathological condition and/or to a stage or degree of a pathological condition.

12. Method according to claim 11 wherein the pathological condition is selected from the group consisting of diabetes, arthritis, elevated cholesterol level, anemia, tissue destruction, cancer, liver diseases, kidney diseases, myocardial infarction, AIDS, allergies, urticaria, allergic asthma, autoimmune diseases, neurodegenerative diseases and TSE.

13. Method according to claim 11 wherein the pathological condition is caused by feed and/or feed additives used in animal husbandry.

14. Method according to claim 1 wherein the biological fluid is selected from the group consisting of blood, blood plasma, blood serum, hemolysate, spinal fluid, urine, saliva, sperm, lymph, synovial fluid, amniotic fluid, lacrimal fluid, cyst fluid, sweat gland secretion and bile.

15. Method according to claim 1 wherein the sample of unknown condition is assigned to the presence of a certain cell type, a certain bacterial strain or a certain viral strain.

16. Method according to claim 1 wherein:
the recording of the IR spectra in step (b) and/or in step (f) is carried out at a wave number from 400 to 7000 cm$^{-1}$;
the recording of the IR spectra in step (b) and/or in step (f) is carried out with the aid of an FTIR spectrometer and/or FTIR microscope;
the recording of the IR spectra in step (b) and/or step (f) is carried out with the aid of a measuring cell with a path length from 3 to 12 μm;
the multiparameter analytical procedure is a discriminatory analysis, a neuronal network or a cluster analysis;
the measuring cell contains integrated electrodes for the reduction and/or oxidation of biomolecules in the sample;
the biological fluid is a body fluid of an organism;
the biological fluid is selected from the group consisting of blood, blood plasma, blood serum, hemolysate, spinal fluid, urine, saliva, sperm, lymph, synovial fluid, amniotic fluid, lacrimal fluid, cyst fluid, sweat gland secretion and bile;
the organism is selected from the group consisting of *Bos taurus, Gallus gallus, Maleagris gallopavo, Mus musculus, Ovis ammon, Rattus norwegicus, Sus scrofa* and *Homo sapiens*;
the sample of unknown condition is assigned to a pathological or non-pathological condition and/or to a stage or degree of a pathological condition;
the pathological condition is selected from the group consisting of diabetes, arthritis, elevated cholesterol level, anemia, tissue destruction, cancer, liver diseases, kidney diseases, myocardial infarction, AIDS, allergies, urticaria, allergic asthma, autoimmune diseases, neurodegenerative diseases and TSE;
the pathological condition is caused by feed and/or feed additives used in animal husbandry;
the sample of unknown condition is assigned to the presence of a certain cell type, a certain bacterial strain or a certain viral strain.

17. Method for preparing a collection of conditions of biological fluids, comprising the steps of
(a) providing several native samples of biological fluids, the condition of each sample of biological fluid being known;
(b) recording the IR spectra of the native samples of step (a);
(c) subjecting the IR spectra of step (b) to a multiparameter analytical procedure and selecting the classification parameters that will ensure a reliable assignment of the samples to the known conditions, and
(d) storing the classification parameters obtained in step (c), wherein the recording of the IR spectra in step (b) is carried out under non-flowing and stopped conditions after filling the flow-through measuring cell with said sample or with a transport medium for a corresponding reference measurement in a measuring cell with a path length of not more than 30 µm and which during the recording of the spectra shows a path length deviation of less than 1 nm between any two consecutive measurements requiring filling or rinsing of said measuring cell between said consecutive measurements, which filling or rinsing can cause flow- or pressure-induced path length deviations.

18. Method according to claim 17 wherein the provision of the native sample(s) in step (a) comprises the homogenization of the biological fluid and/or the freeing of the biological fluid of particulate constituents.

19. Method according to claim 17 wherein:
the recording of the IR spectra in step (b) is carried out at a wave number from 400 to 7000 $cm^{-1}$;
the recording of the IR spectra in step (b) is carried out with the aid of an FTIR spectrometer and/or FTIR microscope;
the recording of the IR spectra in step (b) is carried out with the aid of a measuring cell with a path length from 3 to 12 µm;
the multiparameter analytical procedure is a discriminatory analysis, a neuronal network or a cluster analysis;
the measuring cell contains integrated electrodes for the reduction and/or oxidation of biomolecules in the sample;
the biological fluid is a body fluid of an organism;
the biological fluid is selected from the group consisting of blood, blood plasma, blood serum, hemolysate, spinal fluid, urine, saliva, sperm, lymph, synovial fluid, amniotic fluid, lacrimal fluid, cyst fluid, sweat gland secretion and bile;
the organism is selected from the group consisting of *Bos taurus, Gallus gallus, Maleagris gallopavo, Mus musculus, Ovis ammon, Rattus norwegicus, Sus scrofa* and *Homo sapiens;*
the sample of unknown condition is assigned to a pathological or non-pathological condition and/or to a stage or degree of a pathological condition;
the pathological condition is selected from the group consisting of diabetes, arthritis, elevated cholesterol level, anemia, tissue destruction, cancer, liver diseases, kidney diseases, myocardial infarction, AIDS, allergies, urticaria, allergic asthma, autoimmune diseases, neurodegenerative diseases and TSE;
the pathological condition is caused by feed and/or feed additives used in animal husbandry;
the sample of unknown condition is assigned to the presence of a certain cell type, a certain bacterial strain or a certain viral strain.

20. Method for determining the condition of a biological fluid comprising the steps of
(e) providing a native sample of a biological fluid, the condition of which is unknown;
(f) recording an IR spectrum of the native sample of a biological fluid;
(g) subjecting the IR spectrum of step (f) to a multiparameter analysis; and
(h) comparing the classification parameters of the IR spectrum of the unknown sample with the classification parameters of the IR spectrum of the known sample,
wherein the IR spectra in step (f) are recorded under non-flowing and stopped conditions after filling the flow-through measuring cell with said sample or with a transport medium for a corresponding reference measurement, with the aid of a measuring cell with a path length of not more than 30 µm and which during the recording of the spectra shows a path length deviation of less than 1 nm between any two consecutive measurements requiring filling or rinsing of said measuring cell between said consecutive measurements, which filling or rinsing can cause flow- or pressure-induced path length deviations.

21. Method according to claim 20 wherein the provision of the native sample in step (e) comprises the homogenization of the biological fluid and/or the freeing of the biological fluid of particulate constituents.

22. Method according to claim 20 wherein:
the recording of the IR spectra in step (f) is carried out at a wave number from 400 to 7000 $cm^{-1}$;
the recording of the IR spectra in step (f) is carried out with the aid of an FTIR spectrometer and/or FTIR microscope;
the recording of the IR spectra in step (f) is carried out with the aid of a measuring cell with a path length from 3 to 12 µm;
the multiparameter analytical procedure is a discriminatory analysis, a neuronal network or a cluster analysis;
the measuring cell contains integrated electrodes for the reduction and/or oxidation of biomolecules in the sample;
the biological fluid is a body fluid of an organism;
the biological fluid is selected from the group consisting of blood, blood plasma, blood serum, hemolysate, spinal fluid, urine, saliva, sperm, lymph, synovial fluid, amniotic fluid, lacrimal fluid, cyst fluid, sweat gland secretion and bile;
the organism is selected from the group consisting of *Bos taurus, Gallus gallus, Maleagris gallopavo, Mus musculus, Ovis ammon, Rattus norwegicus, Sus scrofa* and *Homo sapiens;*
the sample of unknown condition is assigned to a pathological or non-pathological condition and/or to a stage or degree of a pathological condition;
the pathological condition is selected from the group consisting of diabetes, arthritis, elevated cholesterol level, anemia, tissue destruction, cancer, liver diseases, kidney diseases, myocardial infarction, AIDS, allergies, urticaria, allergic asthma, autoimmune diseases, neurodegenerative diseases and TSE;
the pathological condition is caused by feed and/or feed additives used in animal husbandry;
the sample of unknown condition is assigned to the presence of a certain cell type, a certain bacterial strain or a certain viral strain.

* * * * *